United States Patent [19]

Levitt

[11] 4,190,432
[45] Feb. 26, 1980

[54] HERBICIDAL SULFONAMIDES

[75] Inventor: George Levitt, Wilmington, Del.

[73] Assignee: E. I. Du Pont de Nemours and Company, Wilmington, Del.

[21] Appl. No.: 820,882

[22] Filed: Aug. 1, 1977

[51] Int. Cl.$^2$ .................. C07D 251/18; C07D 251/52; A01N 9/22; A01N 9/12
[52] U.S. Cl. ........................................ 71/93; 544/206; 544/208; 544/209; 544/207; 544/324; 544/323; 71/92
[58] Field of Search .................... 544/208, 206; 71/93

[56] References Cited

U.S. PATENT DOCUMENTS

3,939,158  2/1976  Begrich .................. 544/211

FOREIGN PATENT DOCUMENTS

121788  2/1967  Netherlands .

*Primary Examiner*—Alan L. Rotman
*Assistant Examiner*—Robert T. Bond

[57] ABSTRACT

N-(heterocyclicaminocarbonyl)arylsulfonamides, such as N-[(4-methoxy-6-methylamino-1,3,5-triazin-2-yl)-aminocarbonyl]benzenesulfonamide, are useful for the regulation of plant growth and as herbicides, particularly for controlling volunteer corn in soybeans.

37 Claims, No Drawings

HERBICIDAL SULFONAMIDES

BACKGROUND OF THE INVENTION

This invention relates to N-(heterocyclicaminocarbonyl)arylsulfonamide agricultural chemicals.

French Pat. No. 1,468,747 discloses the following para-substituted phenylsulfonamides, useful as antidiabetic agents:

R—⟨phenyl⟩—SO$_2$—NH—C(=O)—NH—⟨pyrimidinyl⟩ wherein R=H, halogen, CF$_3$ or alkyl.

Logemann et al. Chem. Ab., 53, 18052 g (1959), disclose a number of sulfonamides, including uracil derivatives and those having the formula:

H$_3$C—⟨phenyl⟩—SO$_2$NHCNHR (with C=O)

wherein R is butyl, phenyl or

⟨pyrimidinyl with R$_1$⟩ and R$_1$ is hydrogen or methyl. When tested for hypoglycemic effect in rats (oral doses of 25 mg/100 g), the compounds in which R is butyl and phenyl were most potent. The others were of low potency or inactive.

Wojciechowski, J. Acta. Polon. Pharm. 19, p. 121–5 (1962) [Chem. Ab., 59 1633 e] describes the synthesis of N-[(2,6-dimethoxypyrimidin-4-yl)aminocarbonyl]-4-methylbenzenesulfonamide:

CH$_3$—⟨phenyl⟩—SO$_2$NH—C(=O)—NH—⟨2,6-dimethoxypyrimidinyl⟩

Based upon similarity to a known compound, the author predicted hypoglycemic activity for the foregoing compound.

Netherlands Pat. No. 121,788, published Sept. 15, 1966, teaches the preparation of compounds of Formula (i), and their use as general or selective herbicides, ⟨structure (i)⟩ wherein
R$_1$ and R$_2$ may independently be alkyl of 1–4 carbon atoms; and
R$_3$ and R$_4$ may independently be hydrogen, chlorine or alkyl of 1–4 carbon atoms.

Compounds of Formula (ii), and their use as antidiabetic agents, are reported in J. Drug Res. 6, 123 (1974).

⟨thiophene⟩—S—SO$_2$NHCNHR (ii)

wherein R is pyridyl.

The presence of undesired vegetation causes substantial damage to useful crops, especially agricultural products that satisfy man's basic food needs, such as soybeans, wheat, and the like. The current population explosion and concomitant world food shortage demand improvements in the efficiency of producing these crops. Prevention or minimizing the loss of a portion of such valuable crops by killing, or inhibiting the growth of undesired vegetation is one way of improving the efficiency.

A wide variety of materials useful for killing, or inhibiting (controlling) the growth of undesired vegetation is available; such materials are commonly referred to as herbicides. The need exists, however, for still more effective herbicides that destroy or retard weeds without causing significant damage to useful crops.

SUMMARY OF THE INVENTION

According to this invention, there is provided compounds of Formula I and their agriculturally suitable salts, suitable agricultural compositions containing them, and methods of using them as selective, as well as general herbicides having both preemergence and postemergence activity. These compounds are highly active herbicides. They are especially useful for controlling weeds in wheat.

R$_1$—SO$_2$NHCNH—⟨heterocycle with W, X, A, Z⟩ (I)

where

R$_1$ is ⟨phenyl with R$_2$, R$_3$, H⟩ or ⟨thiophene⟩

R$_2$ and R$_3$ are independently hydrogen, fluorine, chlorine, bromine, methyl, methoxy, nitro or trifluoromethyl;
W is oxygen or sulfur;
X is —NHCH$_3$ or —N(CH$_3$)$_2$;
Z is methyl or methoxy; and
A is $$\begin{array}{c} C \\ | \\ H \end{array}$$

or N and their agriculturally suitable salts provided that when $R_2$ is nitro or trifluoromethyl, $R_3$ can not be nitro or trifluoromethyl.

Preferred for their high herbicidal activity or favorable cost or both are those compounds of Formula I where independently:

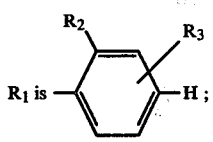

$R_2$ is fluorine, chlorine, bromine, methyl, or nitro; and $R_3$ is hydrogen, fluorine, chlorine, bromine or methyl.

More preferred for their higher herbicidal activity or more favorable cost or both are those compounds of Formula I where

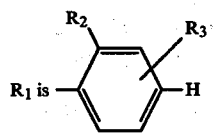

$R_2$ is chlorine, methyl, or nitro; and
$R_3$ is hydrogen, chlorine, or methyl.

Most preferred for their excellent herbicidal activity or more favorable cost or both are those compounds of Formula I where

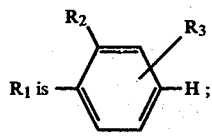

$R_2$ is chlorine, methyl, or nitro;
$R_3$ is hydrogen, chlorine or methyl; and
W is oxygen Specifically preferred for their outstanding herbicidal activity or highly favorable cost or both are:
1. 2-chloro-N-[(4-methoxy-6-methylamino-1,3,5-triazin-2-yl)aminocarbonyl]benzenesulfonamide, m.p. 224°-228° C.;
2. 2-chloro-N-[(4-dimethylamino-6-methoxy-1,3,5-triazin-2-yl)aminocarconyl]benzenesulfonamide, m.p. 200°-206° C.;
3. N-[(4-dimethylamino-6-methoxy-1,3,5-triazin-2-yl)aminocarbonyl]-2-methylbenzenesulfonamide, m.p. 194°-198° C.;
4. N-[(4-methoxy-6-methylamino-1,3,5-triazin-2-yl)aminocarbonyl]-2-methylbenzenesulfonamide, m.p. 199°-202° C.; and
5. N-[(4-dimethylamino-6-methoxypyrimidin-2-yl)aminocarbonyl]-2-methylbenzenesulfonamide, m.p. 238°-239° C.
6. N-[(4-dimethylamino-6-methoxy-1,3,5-triazin-2-yl)aminocarbonyl]-2-nitrobenzenesulfonamide, m.p. 212°-213° C.
7. N-[(4-methylamino-6-methoxy-1,3,5-triazin-2-yl)aminocarbonyl]-2-nitrobenzenesulfonamide.

In addition to having excellent activity for broad spectrum control of vegetation, the compounds of Formula I are also useful for selective control of volunteer corn in soybeans, weeds in wheat, brush control and water hyacinth control. Moreover, the compounds of Formula I are useful plant growth regulants, e.g. increasing sugar content in sugarcane and sorghum and suppressing seed head formation in grasses such as Bahia grass.

SYNTHESIS

As shown in Equation 1, the compounds of Formula I can be prepared by combining an appropriate 2-aminoheterocycle of Formula III with an appropriately substituted sulfonyl isocyanate or isothiocyanate of Formula II; $R_1$, W, X and Z being as previously defined.

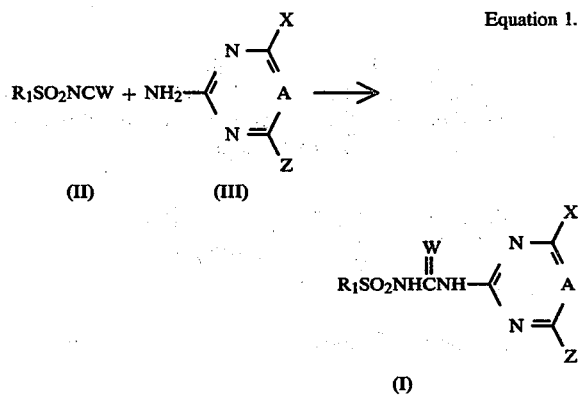

The reaction is best carried out in inert aprotic organic solvents such as methylene chloride, tetrahydrofuran or acetonitrile, at ambient pressure and temperature. The mode of addition is not critical; however, it is often convenient to add the sulfonyl isocyanate or isothiocyanate to a stirred suspension of the aminoheterocycle. Since such isocyanates and isothiocyanates usually are liquids, their addition is more easily controlled.

The reaction is generally exothermic. In some cases, the desired product is insoluble in the warm reaction medium and crystallizes from it in pure form. Products soluble in the reaction medium are isolated by evaporation of the solvent, trituration of the solid residue with solvents such as 1-chlorobutane, ethyl ether, or pentane, and filtration.

The intermediate sulfonyl isocyanates of Formula II (wherein W is O) can be prepared by reacting corresponding sulfonamides with phosgene in the presence of n-butyl isocyanate at reflux in a solvent such as chlorobenzene, according to the procedure of H. Ulrich and A. A. Y. Sayigh, *Newer Methods of Preparative Organic Chemistry*, Vol. VI p 223-241, Academic Press, New York and London, W. Foerst Ed. In cases where formation of the desired sulfonyl isocyanate is difficult by the above procedure the sulfonyl urea formed by reaction of butyl isocyanate with the appropriate sulfonamide is treated with phosgene according to the above reference.

The preparation of sulfonamides from ammonium hydroxide and sulfonyl chlorides is widely reported in the literature, e.g. Crossley et al., *J. Am. Chem. Soc.* 60, 2223 (1938).

Certain sulfonyl chlorides are best prepared by chlorosulfonation of a substituted benzene or thiophene according to the teaching of H. T. Clarke et al. Org. Synth. Coll. Vol. 1, 2nd Ed. 1941, p. 85. Other benzenesulfonyl chlorides are best made by diazotization of the appropriate aniline with sodium nitrite in HCl, followed by reaction of the diazonium salt with sulfur dioxide and cuprous chloride in acetic acid according to the teaching of H. L. Yale and F. Sowinski, J. Org. Chem. 25 1824 (1960).

Sulfonyl isothiocyanates can be prepared by treatment of sulfonamides with carbon disulfide and potassium hydroxide followed by reaction of the dipotassium salt with phosgene according to the teaching of K. Hartke, Arch. Pharm., 299, 174 (1966).

The synthesis of heterocyclic amine derivatives has been reviewed in "The Chemistry of Heterocyclic Compounds", a series published by Interscience Publ., New York and London. 2-Aminopyrimidines are described by D. J. Brown in "The Pyrimidines", Vol. XVI of the above series.

2-Amino-1,3,5-triazines can be synthesized according to methods described by E. M. Smolin and L. Rapoport in "s-Triazines and Derivatives", Vol. XIII, of the same series Agriculturally suitable salts of compounds of Formula I are also useful herbicides and can be prepared in a number of ways known to the art. For example, metal salts can be made by treating compounds of Formula I with a solution of an alkali or alkaline earth metal salt having a sufficiently basic anion (e.g. hydroxide, alkoxide, carbonate or hydride). Quaternary amine salts can be made by similar techniques.

Salts of compounds of Formula I can also be prepared by exchange of one cation for another. Cationic exchange can be effected by direct treatment of an aqueous solution of a salt of a compound of Formula I (e.g. alkali or quaternary amine salt) with a solution containing the cation to be exchanged. This method is most effective when the desired salt containing the exchanged cation is insoluble in water and can be separated by filtration.

Exchange may also be effected by passing an aqueous solution of a salt of a compound of Formula I (e.g. an alkali metal or quaternary amine salt) through a column packed with a cation exchange resin containing the cation to be exchanged. In this method, the cation of the resin is exchanged for that of the original salt and the desired product is eluted from the column. This method is particularly useful when the desired salt is water-soluble.

Acid addition salts, useful in this invention, can be obtained by reacting a compound of Formula I with a suitable acid, e.g. p-toluenesulfonic acid, trichloroacetic acid or the like.

The compounds of this invention and their preparation are further illustrated by the following examples wherein temperatures are given in degrees centigrade and parts are by weight unless otherwise designated.

EXAMPLE 1

2-Chloro-N-[4-methoxy-6-methylamino-1,3,5-triazin-2-yl)-aminocarbonyl]benzenesulfonamide To a solution of 2.1 g of 2-amino-4-methoxy-6-methylamino-1,3,5-triazine in 60 ml of hot acetonitrile was added, dropwise, 3.3 g of 2-chlorobenzenesulfonyl isocyanate in 20 ml of acetonitrile. After stirring for 18 hours at room temperature, the mixture was filtered to yield the product named above melting at 224°–228°.

By using the procedure of Example 1 with equivalent amounts of the appropriate amino-1,3,5-triazine derivative and sulfonyl isocyanate or sulfonylisothiocyanate the compounds of Table I can be prepared.

TABLE I $$\underset{R_3}{\overset{R_2}{\diagdown}}\text{—}SO_2NHCNH\text{—}\underset{N=\underset{Z}{\diagup}}{\overset{N=\overset{X}{\diagdown}}{\diagdown}}$$

(W=O or S double bond on C between NH groups)

| $R_2$ | $R_3$ | W | X | Z | M.P. |
|---|---|---|---|---|---|
| Cl | H | O | $N(CH_3)_2$ | $OCH_3$ | 200°–206° |
| Cl | 5-Cl | O | $N(CH_3)_2$ | $OCH_3$ | 204°–206° |
| Cl | 5-Cl | O | $NHCH_3$ | $OCH_3$ | 219°–228° |
| $CH_3$ | 5-$CH_3$ | O | $NHCH_3$ | $OCH_3$ | 192°–195° |
| $CH_3$ | H | O | $NHCH_3$ | $OCH_3$ | 199°–202° |
| H | H | O | $NHCH_3$ | $OCH_3$ | 281°–286° |
| H | H | O | $N(CH_3)_2$ | $OCH_3$ | 210°–213° |
| F | H | O | $NHCH_3$ | $OCH_3$ | 195°–202° |
| $OCH_3$ | 5-Cl | O | $NHCH_3$ | $OCH_3$ | 198°–203° |
| Cl | 6-Cl | O | $N(CH_3)_2$ | $OCH_3$ | 211°–213° |
| Cl | 5-$CH_3$ | O | $N(CH_3)_2$ | $OCH_3$ | 215°–216° |
| F | H | O | $N(CH_3)_2$ | $OCH_3$ | 183°–186° |
| $OCH_3$ | 5-Cl | O | $N(CH_3)_2$ | $OCH_3$ | 225°–230° |
| $CH_3$ | 5-$CH_3$ | O | $N(CH_3)_2$ | $OCH_3$ | 193°–196° |
| $OCH_3$ | 5-$OCH_3$ | O | $N(CH_3)_2$ | $OCH_3$ | 195°–200° |
| $NO_2$ | H | O | $N(CH_3)_2$ | $OCH_3$ | 212°–213° |
| $NO_2$ | H | O | $NHCH_3$ | $OCH_3$ | |
| Cl | 5-$NO_2$ | O | $N(CH_3)_2$ | $OCH_3$ | |
| $CH_3$ | 5-$NO_2$ | O | $N(CH_3)_2$ | $OCH_3$ | |
| Cl | 3-Cl | O | $N(CH_3)_2$ | $OCH_3$ | |
| $OCH_3$ | 5-$OCH_3$ | O | $NHCH_3$ | $OCH_3$ | |
| $CF_3$ | H | O | $N(CH_3)_2$ | $OCH_3$ | |
| $CH_3O$ | H | O | $N(CH_3)_2$ | $OCH_3$ | |
| H | 3-Cl | O | $NHCH_3$ | $OCH_3$ | |
| H | 3-F | O | $NHCH_3$ | $OCH_3$ | |
| H | 3-$CH_3$ | O | $NHCH_3$ | $OCH_3$ | |
| H | 3-Br | O | $N(CH_3)_2$ | $OCH_3$ | |
| H | 3-$NO_2$ | O | $N(CH_3)_2$ | $OCH_3$ | |
| F | 6-F | O | $N(CH_3)_2$ | $OCH_3$ | |
| F | 5-F | O | $N(CH_3)_2$ | $OCH_3$ | |
| Cl | 5-$CF_3$ | O | $N(CH_3)_2$ | $OCH_3$ | |
| Cl | 5-$NO_2$ | O | $N(CH_3)_2$ | $OCH_3$ | |
| Cl | 5-$CH_3$ | O | $N(CH_3)_2$ | $OCH_3$ | |
| Cl | 5-Cl | S | $N(CH_3)_2$ | $OCH_3$ | |
| Cl | H | S | $N(CH_3)_2$ | $CH_3$ | |
| Cl | 5-Cl | S | $N(CH_3)_2$ | $CH_3$ | |
| Cl | 3-F | O | $NHCH_3$ | $CH_3$ | |
| Br | 5-Br | O | $N(CH_3)_2$ | $CH_3$ | |
| Cl | 6-Cl | S | $N(CH_3)_2$ | $CH_3$ | |
| $CH_3$ | 5-Br | O | $N(CH_3)_2$ | $CH_3$ | |
| $CH_3$ | 5-Cl | O | $N(CH_3)_2$ | $CH_3$ | |
| $CH_3$ | 5-F | O | $N(CH_3)_2$ | $CH_3$ | |
| $OCH_3$ | 5-Cl | S | $N(CH_3)_2$ | $CH_3$ | |
| $OCH_3$ | 5-Cl | O | $N(CH_3)_2$ | $CH_3$ | |
| H | H | O | $N(CH_3)_2$ | $CH_3$ | |
| Cl | H | O | $N(CH_3)_2$ | $CH_3$ | |
| Cl | 5-Cl | O | $N(CH_3)_2$ | $CH_3$ | |
| $OCH_3$ | 5-$OCH_3$ | O | $N(CH_3)_2$ | $CH_3$ | |
| $CH_3$ | 5-$CH_3$ | O | $N(CH_3)_2$ | $CH_3$ | |
| Cl | 6-Cl | O | $N(CH_3)_2$ | $CH_3$ | |
| Br | H | O | $N(CH_3)_2$ | $CH_3$ | |
| $CH_3$ | H | O | $N(CH_3)_2$ | $CH_3$ | |
| $CF_3$ | H | O | $N(CH_3)_2$ | $CH_3$ | |
| $NO_2$ | H | O | $N(CH_3)_2$ | $CH_3$ | |
| F | H | O | $N(CH_3)_2$ | $CH_3$ | |
| F | 6-F | O | $N(CH_3)_2$ | $CH_3$ | |
| Cl | 6-Cl | O | $N(CH_3)_2$ | $CH_3$ | |
| H | H | O | $NHCH_3$ | $CH_3$ | |
| Cl | H | O | $NHCH_3$ | $CH_3$ | |
| Br | H | O | $NHCH_3$ | $CH_3$ | |
| $CH_3$ | H | O | $NHCH_3$ | $CH_3$ | |
| $CF_3$ | H | O | $NHCH_3$ | $CH_3$ | |
| $NO_2$ | H | O | $NHCH_3$ | $CH_3$ | |
| F | H | O | $NHCH_3$ | $CH_3$ | |

EXAMPLE 2

N-[(4-dimethylamino-6-methoxy-1,3,5-triazin-2yl)aminocarbonyl]-2-methylbenzenesulfonamide To a stirred solution of 0.85 g of 2-amino-4-dimethylamino-6-methoxy-1,3,5-triazine in 40 ml of methylene chloride was added, dropwise, 1.0 g of 2-methylbenzenesulfonyl isocyanate in 10 ml of methylene chloride. After stirring 24 hours, the resulting solution was evaporated to yield a solid. Recrystallization from benzene/hexane yielded the product named above melting at 194°–198°.

EXAMPLE 3

N-[(4-dimethylamino-6-methoxy-1,3,5-triazin-2-yl)aminocarbonyl]-2-thiophenesulfonamide To a stirred solution of 1.7 g of 2amino-4-dimethylamino-6-methoxy-1,3,5-triazine in 50 ml of hot acetonitrile was added, dropwise, 1.9 g of thiophenesulfonyl isocyanate in 10 ml of acetonitrile. After stirring for 18 hours, the mixture was filtered to yield 2.0 g of the product named above melting at 192°–195°.

By using this procedure of Example 3, N-[(4-methoxy-6-methylamino-1,3,5-triazin-2-yl)-aminocarbonyl]-2-thiophenesulfonamide was prepared melting at 208°–210°.

EXAMPLE 4

N-[(4-methoxy-6-methylamino-1,3,5-triazin-2yl)aminocarbonyl]-2-thiophenesulfonamide, sodium salt To a slurry of 2.5 g of N-[(4-methoxy-6-methylamino-1,3,5-triazin-2-yl)-aminocarbonyl]-2-thiophenesulfonamide and 50 ml of water was added 3 ml of 10% sodium hydroxide. The resulting solution was filtered and after cooling the filtrate, a white crystalline solid formed. Filtration afforded 1.1 g of the product named above melting at 297°–298°.

EXAMPLE 5

N-[(4-dimethylamino-6-methylpyrimidin-2-yl)aminocarbonyl]-benzenesulfonamide

To a suspension of 15.2 g of 2-amino-4-dimethylamino-6-methylpyrimidine in 400 ml of methylene chloride at ambient temperature was added slowly 18.3 g of benzenesulfonylisocyanate. After stirring for four hours the mixture was stripped in-vacuo and the white semisolid residue triturated with ethyl ether and isolated by filtration. The solid was then slurried in hot acetone, cooled and refiltered to yield the solid named above which decomposed at 180°–182°.

EXAMPLE 6

2-Chloro-N-[(4-dimethylamino-6-methoxypyrimidin-2yl)aminocarbonyl]benzenesulfonamide To 700 ml of acetonitrile containing 25 g of 2-amino-4-dimethylamino-6-methoxypyrimidine at ambient temperature was added dropwise 32.5 g of 2-chlorobenzenesulfonylisocyanate. The mixture was warmed to 40° and then allowed to stir for five hours at ambient temperature. The solid product named above was isolated by filtration and washed with a small amount of cold ethyl ether. It melted at 224°–226°.

By using the procedure of Example 6 with equivalent amounts of the appropriate 2-aminopyrimidine derivative and sulfonylisocyanate the compounds of Table II can be prepared.

TABLE II

| R₂ | R₃ | W | X | Z | M.P. |
|---|---|---|---|---|---|
| H | H | O | N(CH₃)₂ | OCH₃ | |
| H | H | S | N(CH₃)₂ | OCH₃ | |
| CH₃ | H | O | N(CH₃)₂ | OCH₃ | 238°–239° |
| Cl | H | O | N(CH₃)₂ | OCH₃ | 224°–226° |
| F | H | O | N(CH₃)₂ | OCH₃ | |
| Br | H | O | N(CH₃)₂ | OCH₃ | |
| NO₂ | H | O | N(CH₃)₂ | OCH₃ | |
| OCH₃ | H | O | N(CH₃)₂ | OCH₃ | |
| CF₃ | H | O | N(CH₃)₂ | OCH₃ | |
| Cl | H | S | N(CH₃)₂ | OCH₃ | |
| CH₃ | H | S | N(CH₃)₂ | OCH₃ | |
| F | H | S | N(CH₃)₂ | OCH₃ | |
| Cl | 6-Cl | O | NHCH₃ | OCH₃ | |
| Cl | 5-CH₃ | O | NHCH₃ | OCH₃ | |
| Cl | 5-CF₃ | O | N(CH₃)₂ | OCH₃ | |
| Cl | 5-Br | O | NHCH₃ | OCH₃ | |
| Cl | 3-Cl | O | NHCH₃ | OCH₃ | |
| Cl | 3-F | O | NHCH₃ | OCH₃ | |
| OCH₃ | 5-OCH₃ | O | NHCH₃ | OCH₃ | |
| H | 3-Cl | O | NHCH₃ | OCH₃ | |
| H | 3-F | O | NHCH₃ | OCH₃ | |
| H | 3-NO₂ | O | N(CH₃)₂ | OCH₃ | |
| Cl | 5-Cl | S | N(CH₃)₂ | OCH₃ | |
| Cl | 3-Cl | S | N(CH₃)₂ | OCH₃ | |
| Cl | 5-F | S | N(CH₃)₂ | OCH₃ | |
| Cl | 5-OCH₃ | S | N(CH₃)₂ | OCH₃ | |
| H | H | O | N(CH₃)₂ | CH₃ | |
| Cl | H | O | N(CH₃)₂ | CH₃ | |
| Br | H | O | N(CH₃)₂ | CH₃ | |
| F | H | O | N(CH₃)₂ | CH₃ | |
| CH₃ | H | O | N(CH₃)₂ | CH₃ | |
| CF₃ | H | O | N(CH₃)₂ | CH₃ | |
| NO₂ | H | O | N(CH₃)₂ | CH₃ | |
| OCH₃ | H | O | N(CH₃)₂ | CH₃ | |
| Cl | 5-Cl | O | N(CH₃)₂ | CH₃ | |
| Cl | 6-Cl | O | N(CH₃)₂ | CH₃ | |
| Br | 5-Br | O | N(CH₃)₂ | CH₃ | |
| OCH₃ | 5-OCH₃ | O | N(CH₃)₂ | CH₃ | |
| CH₃ | 5-CH₃ | O | N(CH₃)₂ | CH₃ | |
| Cl | 3-Cl | O | N(CH₃)₂ | CH₃ | |
| CH₃ | 5-NO₂ | O | N(CH₃)₂ | CH₃ | |
| OCH₃ | 5-Cl | O | NHCH₃ | CH₃ | |
| Cl | 5-NO₂ | O | N(CH₃)₂ | CH₃ | |
| Cl | 5-F | O | NHCH₃ | CH₃ | |
| H | 3-CH₃ | O | N(CH₃)₂ | CH₃ | |
| H | 3-Br | O | N(CH₃)₂ | CH₃ | |
| H | H | O | NHCH₃ | CH₃ | |
| Cl | H | O | NHCH₃ | CH₃ | |
| Br | H | O | NHCH₃ | CH₃ | |
| F | H | O | NHCH₃ | CH₃ | |
| CH₃ | H | O | NHCH₃ | CH₃ | |
| CF₃ | H | O | NHCH₃ | CH₃ | |
| NO₂ | H | O | NHCH₃ | CH₃ | |
| OCH₃ | H | O | NHCH₃ | CH₃ | |
| Cl | 5-Cl | O | NHCH₃ | CH₃ | |
| Cl | 6-Cl | O | NHCH₃ | CH₃ | |
| Br | 5-Br | O | NHCH₃ | CH₃ | |
| OCH₃ | 5-OCH₃ | O | NHCH₃ | CH₃ | |
| CH₃ | 5-CH₃ | O | NHCH₃ | CH₃ | |
| Cl | 3-Cl | O | NHCH₃ | CH₃ | |
| CH₃ | 5-NO₂ | O | NHCH₃ | CH₃ | |
| NO₂ | H | O | NHCH₃ | OCH₃ | |

FORMULATIONS

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid diluent(s). More specifically, they will contain these ingredients in the following approximate proportions:

TABLE III

|  | Active Ingredient | Diluent(s) | Surfactant(s) |
| --- | --- | --- | --- |
| Wettable Powders | 20–90 | 0–74 | 1–10 |
| Oil Suspensions, Emulsions, Solutions (including Emulsifiable Concentrates) | 3–50 | 40–95 | 0–15 |
| Aqueous Suspensions | 10–50 | 40–84 | 1–20 |
| Dusts | 1–25 | 70–99 | 0–5 |
| Granules and Pellets | 0.1–95 | 5–99.9 | 0–15 |
| High Strength Compositions | 90–99 | 0–10 | 0–2 |

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J. The more absorptive diluents are preferred for wettable powders and the denser ones for dusts. Typical liquid diluents and solvents are described in Marsden, "Solvents Guide", 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, New Jersey, as well as Sisely and Wood, "Encyclopedia of Surface Active Agents", Chemical Publishing Co., Inc., New York, 1964, list surfactants and recommended uses. All formulations can contain minor amounts of additives to reduce foam, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering*, Dec. 4, 1967, pp. 147ff. and "Perry's Chemical Engineer's Handbook", 4th Ed., McGraw-Hill, New York, 1963, pp. 8–59 ff.

For further information regarding the art of formulation, see for example:

H. M. Loux, U.S. Pat. No. 3,235,361, Feb. 15, 1966, Col. 6, line 16 through Col. 7, line 19 and Examples 10 through 41.

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138–140, 162–164, 166, 167, 169–182.

H. Gysin and E. Knusli, U.S. Pat. No. 2,891,855, June 23, 1959, Col. 3, line 66 through Col. 5, line 17 and Examples 1–4.

G. C. Klingman, "Weed Control as a Science", John Wiley & Sons, Inc., New York, 1961, pp. 81–96.

J. D. Fryer and S. A. Evans, "Weed Control Handbook", 5th Ed., Blackwell Scientific Publications, Oxford, 1968, pp. 101–103.

In the following examples, all parts are by weight unless otherwise indicated.

EXAMPLE 7

| Wettable Powder | |
| --- | --- |
| 2-chloro-N-[(4-methoxy-6-methylamino-1,3,5-triazin-2-yl)aminocarbonyl]benzenesulfonamide | 80% |
| sodium alkylnaphthalenesulfonate | 2% |
| sodium ligninsulfonate | 2% |
| synthetic amorphous silica | 3% |
| kaolinite | 13% |

The ingredients are blended, hammer-milled until all the solids are essentially under 50 microns, reblended, and packaged.

EXAMPLE 8

| Wettable Powder | |
| --- | --- |
| 2-chloro-N-[(4-dimethylamino-6-methoxy-1,3,5,-triazin-2-yl)aminocarbonyl]-benzenesulfonamide | 50% |
| sodium alkylnaphthalenesulfonate | 2% |
| low viscosity methyl cellulose | 2% |
| diatomaceous earth | 46% |

The ingredients are blended, coarsely hammer-milled and then air-milled to produce particles essentially all below 10 microns in diameter. The product is reblended before packaging.

EXAMPLE 9

| Granule | |
| --- | --- |
| wettable powder of Example 8 | 5% |
| attapulgite granules (U.S.S. 20–40 mesh; 0.84–0.42 mm) | 95% |

A slurry of wettable powder containing ≈25% solids is sprayed on the surface of attapulgite granules in a double-cone blender. The granules are dried and packaged.

EXAMPLE 10

| Extruded Pellets | |
| --- | --- |
| N-[4-dimethylamino-6-methoxypyrimidin-2-yl) aminocarbonyl]-2-methylbenzenesulfonamide | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammermilled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 11

| Oil Suspension | |
|---|---|
| 2-chloro-N-[(4-dimethylamino-6-methoxy-1,3,5-triazin-2-yl)aminocarbonyl]benzenesulfonamide | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting suspension may be applied directly, but preferably after being extended with oils or emulsified in water.

EXAMPLE 12

| Wettable Powder | |
|---|---|
| N-[(4-dimethylamino-6-methoxy-1,3,5-triazin-2-yl)aminocarbonyl]-2-methylbenzenesulfonamide | 20% |
| sodium alkylnaphthalenesulfonate | 4% |
| sodium ligninsulfonate | 4% |
| low viscosity methyl cellulose | 3% |
| attapulgite | 69% |

The ingredients are thoroughly blended. After grinding in a hammer mill to produce particles essentially all below 100 microns, the material is reblended and sifted through a U.S.S. No. 50 sieve (0.3 mm opening) and packaged.

EXAMPLE 13

| Oil Suspension | |
|---|---|
| 2-chloro-N-[(4-methoxy-6-methylamino-1,3,5-triazin-3-yl)aminocarbonyl]benzenesulfonamide | 35% |
| blend of polyalcohol carboxylic esters and oil soluble petroleum sulfonates | 6% |
| xylene | 59% |

The ingredients are combined and ground together in a sand mill to produce particles essentially all below 3 microns. The product can be used directly, extended with oils, or emulsified in water.

EXAMPLE 14

| High Strength Concentrate | |
|---|---|
| N-[(4-dimethylamino-6-methoxypyrimidin-2-yl)aminocarbonyl]-2-methylbenzenesulfonamide | 99% |
| silica aerogel | 0.5% |
| synthetic amorphous silica | 0.5% |

The ingredients are blended and ground in a hammer mill to produce a material essentially all passing a U.S.S. No. 50 screen (0.3 mm opening). The concentrate may be formulated further if necessary.

EXAMPLE 15

| Low Strenght Granule | |
|---|---|
| N-[(4-dimethylamino-6-methoxy-1,3,5-triazin-2-yl)aminocarbonyl]-2-methylbenzenesulfonamide | 1% |
| N,N-dimethylformamide | 9% |
| attapulgite granules (U.S.S. 20-40 mesh). | 90% |

The active ingredient is dissolved in the solvent and the solution is sprayed upon dedusted granules in a rotating blender. After spraying of the solution has been completed, the blender is allowed to run for a short period and then the granules are packaged.

EXAMPLE 16

| Aqueous Suspension | |
|---|---|
| N-[(4-dimethylamino-6-methoxy-1,3,5-triazin-2-yl)aminocarbonyl]-2-methylbenzenesulfonamide | 40% |
| polyacrylic acid thickener | 0.3% |
| dodecylphenol polyethylene glycol ether | 0.5% |
| disodium phosphate | 1.0% |
| monosodium phosphate | 0.5% |
| polyvinyl alcohol | 1.0% |
| water | 56.7% |

The ingredients are blended and ground together in a sand mill to produce particles essentially all under 5 microns in size.

EXAMPLE 17

| Solution | |
|---|---|
| N-[(4-methoxy-6-methylamino-1,3,5-triazin-2-yl)aminocarbonyl]-2-methylbenzenesulfonamide, sodium salt | 5% |
| water | 95% |

The salt is added directly to the water with stirring to produce the solution, which may then be packaged for use.

EXAMPLE 18

| Granule | |
|---|---|
| 2-chloro-N-[(4-methoxy-6-methylamino-1,3,5-triazin-2-yl)aminocarbonyl]benzenesulfonamide | 80% |
| wetting agent | 1% |
| crude ligninsulfonate salt (containing 5-20% of the natural sugars) | 10% |
| attapulgite clay | 9% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14-100 mesh (1410-149 microns), and packaged for use.

EXAMPLE 19

| Low Strength Granule | |
|---|---|
| N-[(4-methoxy-6-methylamio-1,3,5-triazin-2-yl)-aminocarbonyl]-2-methylbenzenesulfonamide | 0.1% |
| attapulgite granules (U.S.S) 20–40 mesh | 99.9% |

The active ingredient is dissolved in a solvent and the solution is sprayed upon dedusted granules in a double cone blender. After spraying of the solution has been completed, the material is warmed to evaporate the solvent. The material is allowed to cool and then packaged.

EXAMPLE 20

| Wettable Powder | |
|---|---|
| N-[(4-dimethylamino-6-methoxypyrimidin-2-yl)-aminocarbonyl]-2-methylbenzene-sulfonamide | 95% |
| dioctyl sodium sulfosuccinate | 0.1% |
| synthetic fine silica | 4.9% |

The ingredients are blended and ground in a hammer mill to produce particles essentially all below 100 microns. The material is sifted through a U.S.S. No. 50 screen and then packaged.

EXAMPLE 21

| Wettable Powder | |
|---|---|
| N-[(4-methoxy-6-methylamino-1,3,5-triazin-2-yl)aminocarbonyl]-2-methylbenzene-sulfonamide | 40% |
| sodium ligninsulfonate | 20% |
| montmorillonite clay | 40% |

The ingredients are thoroughly blended, coarsely hammermilled and then air-milled to produce particles essentially all below 10 microns in size. The material is reblended and then packaged.

The compounds of Formula I can be formulated using the procedures of Examples 7–21.

UTILITY

The compounds of Formula I are useful as herbicides. They may be applied either pre- or postemergence for the control of undesired vegetation in noncrop areas or for selective weed control in certain crops, e.g., wheat and soybeans. By properly selecting rate and time of application, compounds of this invention may be used to modify plant growth beneficially.

The precise amount of the compound of Formula I to be used in any given situation will vary according to the particular end result desired, the use involved, the weeds to be controlled, the soil type, the formulation and mode of application, weather conditions, etc. Since so many variables play a role, it is not possible to state a rate of application suitable for all situations. Broadly speaking, the compounds of this invention are used at levels of about 0.01 to 20 kg/ha with a preferred range of 0.1 to 10 kg/ha. The lower rates of the range will generally be selected for lighter soils, for selective weed control in crops, or in situations where maximum persistence is not necessary. Some of the compounds of Formula I can be used at very low rates for plant growth modification, but higher rates may also be useful, depending on factors such as the crop being treated, timing of treatment, etc.

The compounds of Formula I may be combined with other herbicides and are particularly useful in combination with 3-(3,4-dichlorophenyl)-1,1-dimethylurea, the triazines such as 2-chloro-4-(ethylamino)-6-(isopropylamino)-s-triazine, the uracils such as 5-bromo-3-sec-butyl-6-methyluracil, N-(phosponomethyl)glycine, 3-cyclohexyl-1-methyl-6-dimethylamino-s-triazine-2,4(1H,3H)-dione, N,N-dimethyl-2,2-diphenylacetamide, 2,4-dichlorophenoxyacetic acid (and closely related compounds), 4-chloro-2-butynyl-3-chlorophenylcarbamate, diisopropylthiolcarbamic acid, ester with 2,3-dichloroallyl alcohol, diisopropylthiolcarbamic acid, S-(2,3,3-trichloroallyl)ester, ethyl-N-benzoyl-N-(3,4-dichlorophenyl)-2-aminopropionate, 1,2-dimethyl-3,5-diphenylpyrazolium methylsulfate, methyl 2-[4-(2,4-dichlorophenoxy)-phenoxy]-propanoate, 4-amino-6-tert-butyl-3-(methylthio)-1,2,4-triazin-5(4H)-one, 3-(3,4-dichlorophenyl)-1-methoxy-1-methylurea, 3-isopropyl-1H-2,1,3-benzothiodiazin-(4)-3H-one 2,2-dioxide, $\alpha,\alpha,\alpha$-trifluoro-2,6-dinitro-N,N-dipropyl-p-toluidine, 1,1'-dimethyl-4,4'-bipyridinium ion, monosodium methanearsonate, 2-chloro-2',6'-diethyl(methoxymethyl)acetanilide, and 1,1-dimethyl-3-($\alpha,\alpha,\alpha$-trifluoro-m-tolyl)-urea.

The activity of these compounds was discovered in greenhouse tests. The tests are described and the data resulting from them are shown below.

TEST PROCEDURE

Seeds of crabgrass (Digitaria sp.), barnyardgrass (Echinochloa crusgalli), wild oats (Avena fatua), Cassia tora, morningglory (Ipomoea sp.), cocklebur (Xanthium sp.), sorghum, corn, soybean, rice, wheat and nutsedge tubers were planted in a growth medium and treated preemergence with the chemicals dissolved in a non-phytotoxic solvent, At the same time, cotton having five leaves (including cotyledonary ones), bush beans with the third trifoliolate leaf expanding, crabgrass with two leaves, barnyardgrass with two leaves, wild oats with one leaf, cassia with three leaves (including cotyledonary ones), morningglory with four leaves (including the cotyledonary ones), cocklebur with four leaves (including the cotyledonary ones), sorghum with three leaves, corn with three leaves, soybean with two cotyledonary leaves, rice with two leaves, wheat with one leaf, and nutsedge with three-five leaves were sprayed. Treated plants and controls were maintained in a greenhouse for 16 days, then all species were compared to controls and visually rated for response to treatment.

Ratings for compounds tested by this procedure are recorded in Table III.

O=no effect
& or 10=maximum effect
C=chlorosis or necrosis
E=emergence inhibition
G=growth retardation
H=formative effects
S=albinism
U=unusual pigmentation
6Y=abscised buds or flowers

TABLE III $$R_1-SO_2NHCNH-\underset{N}{\overset{N}{\underset{Z}{\bigvee}}}\underset{A}{\overset{X}{\bigvee}}$$

| $R_1$ | A | X | Z | Rate, kg/ha | Bush Bean | Cotton | Sorghum | Corn | Soybeans | Postemergence Wheat | Wild Oats | Rice | Barnyardgrass | Crabgrass | Morningglory |
|---|---|---|---|---|---|---|---|---|---|---|---|---|---|---|---|
| 2,5-(OCH₃)₂-C₆H₃ | N | N(CH₃)₂ | OCH₃ | 2.0 | 3S | 4C | 2U | 5U | 2C | 3C | 7G | 3C | 2C | 2C | 2C |
|  |  |  |  | 2.0 | 8G | 7G | 8G | 9G | 3H | 8G |  | 7G | 8H | 7G |  |
|  |  |  |  | 2.0 | 6Y |  | 8G |  |  |  |  |  |  |  |  |
|  |  |  |  | 0.4 | 3S | 2C | 2U | 8G | 3C | 2C | 8G | 4C | 7G | 5G | 2C |
|  |  |  |  | 0.4 | 7G | 3H | 8G |  | 8G | 9G |  | 8G |  |  | 7G |
|  |  |  |  | 0.4 | 6Y | 8G |  |  |  |  |  |  |  |  |  |
| 2-CH₃-C₆H₄ | N | NHCH₃ | OCH₃ | 0.4 | 4C | 5C | 5U | 5C | 3H | 2C | 2C | 5C | 9H | 8G | 10C |
|  |  |  |  | 0.4 | 9G | 9G | 9G | 9G | 9G |  | 8G | 9G |  |  |  |
|  |  |  |  | 0.4 |  |  |  |  |  |  |  |  |  |  |  |
| 2-CH₃-C₆H₄ | N | N(CH₃)₂ | OCH₃ | 0.4 | 6C | 5C | 2U | 1C | 3C | 2C | 1C | 5C | 2C | 2C | 10C |
|  |  |  |  | 0.4 | 9G | 9G | 9G | 9G | 9G | 7G | 8H | 8G | 9H | 6G |  |
| 2-Cl-C₆H₄ | N | N(CH₃)₂ | OCH₃ | 0.4 | 9C | 2C | 2U | 9G | 2C | 8G | 1C | 5C | 6C | 5C | 10C |
|  |  |  |  | 0.4 |  | 9G | 9G |  | 9G |  | 8G | 8G | 9H | 9G |  |
| 2-Cl-C₆H₄ | N | NHCH₃ | OCH₃ | 0.4 | 4H | 5H | 6G | 5G | 5C | 4G | 4G | 4C | 3C | 7C | 8C |
|  |  |  |  |  | 7G | 4G |  |  | 5G |  |  | 4G |  |  |  |
| 2,4-(CH₃)₂-C₆H₃ | N | NHCH₃ | OCH₃ | 0.4 | 5C | 5C | 3G | 0 | 3C | 2G | 0 | 4G | 2C | 2C | 10C |
|  |  |  |  | 0.4 | 4G | 3G |  |  | 5G |  |  |  |  |  |  |
|  |  |  |  | 0.4 | 6Y |  |  |  |  |  |  |  |  |  |  |
| C₆H₅ | N | NHCH₃ | OCH₃ | 0.4 | 5C | 4C | 3C | 1G | 2C | 2G | 2G | 5G | 1C | 1C | 2C |
|  |  |  |  | 0.4 | 4G | 2G | 2G |  | 2G |  |  |  |  |  |  |
|  |  |  |  | 0.4 | 6Y |  |  |  |  |  |  |  |  |  |  |
| C₆H₅ | N | N(CH₃)₂ | OCH₃ | 0.4 | 5C | 5C | 1C | 0 | 1C | 0 | 0 | 4G | 1C | 0 | 1G |
|  |  |  |  | 0.4 | 3G | 3G |  |  |  |  |  |  |  |  |  |
|  |  |  |  | 0.4 | 6Y |  |  |  |  |  |  |  |  |  |  |
| 4-Cl-2-OCH₃-C₆H₃ | N | NHCH₃ | OCH₃ | 0.4 | 4C | 2C | 0 | 0 | 0 | 0 | 0 | 0 | 0 | 0 | 0 |
|  |  |  |  | 0.4 | 3G |  |  |  |  |  |  |  |  |  |  |
|  |  |  |  | 0.4 | 6Y |  |  |  |  |  |  |  |  |  |  |
| 2,4-Cl₂-C₆H₃ | N | N(CH₃)₂ | OCH₃ | 0.4 | 8C | 2C | 5G | 4G | 2C | 3G | 3G | 1C | 3C | 2C | 10C |
|  |  |  |  | 0.4 | 9G | 7G |  |  | 7G |  |  | 5G | 7G | 5G |  |
| 2,6-Cl₂-C₆H₃ | N | N(CH₃)₂ | OCH₃ | 0.4 | 5C | 2H | 7C | 5C | 5C | 9C | 6C | 9C | 9C | 2C | 9C |
|  |  |  |  | 0.4 | 9G | 3C | 9G | 9G | 9G |  | 8G |  | 9G | 8G |  |
|  |  |  |  | 0.4 |  | 9G |  |  |  |  |  |  |  |  |  |
| 2-Cl-5-CH₃-C₆H₃ | N | N(CH₃)₂ | OCH₃ | 0.4 | 3C | 3C | 8H | 5G | 3H | 3G | 2G | 8G | 2C | 3G | 10C |
|  |  |  |  | 0.4 | 8G | 6G |  |  |  |  |  |  | 8H |  |  |
|  |  |  |  | 0.4 | 6Y |  |  |  |  |  |  |  |  |  |  |
| 2-F-C₆H₄ | N | N(CH₃)₂ | OCH₃ | 0.4 | 3C | 6C | 3H | 5C | 4C | 2C | 7G | 9C | 3C | 9C | 10C |
|  |  |  |  | 0.4 | 9G | 9G | 8G | 9G | 8G | 7G |  |  | 9H |  |  |
|  |  |  |  | 0.4 | 6Y |  |  |  |  |  |  |  |  |  |  |
| 4-Cl-2-OCH₃-C₆H₃ | N | N(CH₃)₂ | OCH₃ | 0.4 | 3C | 2C | 2C | 4G | 3H | 4G | 3G | 6G | 3C | 1C | 1C |
|  |  |  |  | 0.4 | 4H | 6G | 8G |  |  |  |  |  |  |  |  |
|  |  |  |  | 0.4 | 6F |  |  |  |  |  |  |  |  |  |  |

TABLE III-continued

| R1 | A | X | Z | Rate, kg/ha | Sorghum | Corn | Soybeans | Wheat | Wild Oats | Rice | Barnyardgrass | Crabgrass | Morningglory | Cocklebur | Cassia | Nutsedge |
|---|---|---|---|---|---|---|---|---|---|---|---|---|---|---|---|---|
| 2-thienyl | N | N(CH₃)₂ | OCH₃ | 0.4<br>0.4<br>0.4 | 2H<br>8G<br>6Y | 4C<br>7G | 2C<br>6G | 9H | 4C<br>8G | | 1C<br>3G | 2C<br>8G | 7C | 1C<br>4G | 3C<br>9G | |
| 2,4-(CH₃)₂-phenyl | N | N(CH₃)₂ | OCH₃ | 0.4<br>0.4<br>0.4 | 3C<br>8G<br>6Y | 3C<br>6G | 2C<br>7G | 7H | 5C<br>8G | 5G | 4G | 1C<br>7G | 2C<br>8G | 3G | 5C<br>9G | |
| 2-CH₃-phenyl | CH | N(CH₃)₂ | OCH₃ | 2.0<br>2.0<br>2.0 | 2S<br>5G<br>6Y | 3C<br>3H | 2U<br>9G | 2U<br>9G | 3C<br>3H | 4C<br>9G | 2C<br>8G | 3C<br>6G | 3C<br>9H | 3C<br>7G | 2C | |
| 2-thienyl | N | NHCH₃ | OCH₃ | 0.4<br>0.4<br>0.4 | 3C<br>8G<br>6Y | 3C<br>8G | 2C<br>7G | 8H<br>5G | 2C | 4G | 3G | 2C<br>5G | 1C<br>5G | 6C | 2C<br>3H | |
| 2-F-phenyl | N | NHCH₃ | OCH₃ | 0.4<br>0.4<br>0.4 | 3C<br>8G<br>6Y | 4C<br>8G | 2C<br>8G | 3U<br>8G | 5C<br>7G | 2G | 6G | 5C<br>7G | 3C<br>7G | 3C | 2C<br>6G | |
| 2-NO₂-phenyl | N | N⁺H(CH₃)₂ Na⁺ | OCH₃ | 0.4<br>0.4 | 9C | 9C | 5U<br>9G | 9C | 3C<br>9G | 7C<br>8G | 9C | 9C | 10C | 10C | 10C | |

$$R_1-SO_2NHCNH-\underset{Z}{\overset{N}{\underset{\|}{\bigvee}}}\overset{X}{\underset{A}{\bigwedge}}$$

Preemergence

| R1 | A | X | Z | Rate, kg/ha | Sorghum | Corn | Soybeans | Wheat | Wild Oats | Rice | Barnyardgrass | Crabgrass | Morningglory | Cocklebur | Cassia | Nutsedge |
|---|---|---|---|---|---|---|---|---|---|---|---|---|---|---|---|---|
| 2,6-(OCH₃)₂-phenyl | N | N(CH₃)₂ | OCH₃ | 2.0<br>2.0<br>2.0<br>0.4<br>0.4<br>0.4 | 2U<br>9G<br>2U<br>9G | 9G<br>10E | 5H<br>8H | 9G<br>9G | 9G<br>2C<br>8G | 10E<br>10E | 9H<br>9H | 9G<br>9G | 9C<br>9C | 9H<br>9G | 8G<br>1C<br>9G | 9G<br>8G |
| 2-CH₃-phenyl | N | NHCH₃ | OCH₃ | 0.4<br>0.4<br>0.4 | 9H | 10E | 8H | 9H | 8G | 10E | 9H | 6G | 9G | 9G | 9G | 8G |
| 2-CH₃-phenyl | N | N(CH₃)₂ | OCH₃ | 0.4<br>0.4 | 9H | 10E | 9H | 9H | 8G | 10E | 9C | 8G | 9G | 8G | 9G | 5G |
| 2-Cl-phenyl | N | N(CH₃)₂ | OCH₃ | 0.4<br>0.4 | 9H | 9G | 8H | 2C<br>8G | 2C<br>8G | 10E | 9H | 2C<br>9G | 8G | 8G | 7G | 9G |
| 2-Cl-phenyl | N | NHCH₃ | OCH₃ | 0.4 | 10E | 8G | 7C<br>3G | 3G | 3G | 10E | 6G | 10E | 8G | 10E | 4G | 5G |
| 2,4-(CH₃)₂-phenyl | N | NHCH₃ | OCH₃ | 0.4<br>0.4<br>0.4 | 5G | 2G | 1G | 1G | 2G | 8G | 2G | 1G | 3G | 2G | 3G | 3G |
| phenyl | N | NHCH₃ | OCH₃ | 0.4<br>0.4<br>0.4 | 5G<br>5C | 2G | 1G | 2G | 3G | 9C | 3C | 1G | 3G | 10E | 2G | 2G |
| phenyl | N | N(CH₃)₂ | OCH₃ | 0.4<br>0.4<br>0.4 | 4C<br>5G | 2C | 1C | 4G | 2G | 10E | 2C | 0 | 5C | 3C | 2C | 0 |
| 4-Cl-2-OCH₃-phenyl | N | NHCH₃ | OCH₃ | 0.4<br>0.4<br>0.4 | 3C<br>6G | 2C<br>3G | 2C<br>2G | 1C | 2C | 10E | 3C | 0 | 7C | 2C | 2C | 0 |

TABLE III-continued

| Structure | Rate | | | | | | | | | | | |
|---|---|---|---|---|---|---|---|---|---|---|---|---|
| 2,6-Cl₂-C₆H₃—N(N(CH₃)₂)(OCH₃) | 0.4 0.4 | 3C | 3G | 0 | 5G | 7G 9H | 1C 6G | 2C | 0 | 7G | 5G | 0 | 0 |
| 2,4-Cl₂-C₆H₃—N(N(CH₃)₂)(OCH₃) | 0.4 0.4 0.4 | 9H | 1C 8H | 8H | 9H | 2C 6G | 10E | 9H | 2C 7G | 9C | 10E | 7G | 10E |
| 2-Cl-6-CH₃-C₆H₃—N(N(CH₃)₂)(OCH₃) | 0.4 0.4 0.4 | 9G | 1C 5G | 0 | 6G | 7G | 10E | 9H | 0 | 9G | 8G | 0 | 5G |
| 2-F-C₆H₄—N(N(CH₃)₂)(OCH₃) | 0.4 0.4 0.4 | 9G | 2C 8G | 1H | 7G | 5G | 10E | 9C | 5G | 5G | 7G | 6G | 8G |
| 2-OCH₃-C₆H₄—N(N(CH₃)₂)(OCH₃) | 0.4 0.4 0.4 | 1C 7G | 0 | 0 | 3C 6G | 6G | 9H | 3G | 4G | 7G | 0 | 1C | 0 |
| 2-Cl-thienyl—N(N(CH₃)₂)(OCH₃) | 0.4 0.4 0.4 | 2C 8G | 1C 7G | 0 | 3G | 6G | 10E | 9H | 1C 7G | 9G | 7G | 5H | 9G |
| 2-CH₃-C₆H₄—N(N(CH₃)₂)(OCH₃) | 0.4 0.4 0.4 | 1C 8G | 2C 7G | 2H | 4G | 6G | 9H | 9H | 2G | 7G | 7G | 3H | 5G |
| 2,6-(CH₃)₂-C₆H₃—CH(N(CH₃)₂)(OCH₃) | 2.0 2.0 2.0 | 2C 9G | 1C 9G | 2C 6H | 9G | 2C 8G | 10E | 9H | 2C | 9G | 8G | 8G | 10E |
| thienyl—N(NHCH₃)(OCH₃) | 0.4 0.4 0.4 | 9G | 9G | 1H | 5G | 6G | 10E | 9H | 8G | 9G | 10E | 7G | 10E |
| 2-F-C₆H₄—N(NHCH₃)(OCH₃) | 0.4 0.4 | 9H | 2C 9G | 2H | 1C 8G | 2C 5G | 10E | 9H | 2C 9G | 9G | 9C | 8G | 9G |
| 2-NO₂-C₆H₄—N(Na⊕)(H(CH₃)₂)(OCH₃) | 0.4 0.4 | 2U 9G | 10E | 9G | 9G | 3C 9H | 10E | 9C | 5C 9G | 9G | 9G | 9G | 10E |

Utility of the compounds of the invention for selective weed control in wheat and soybeans was first observed in greenhouse tests. The test described below (B) illustrates these utilities.

TEST B

Two 25 cm diameter plastic bulb pans were filled with fertilized and limed Fallsington silt loam soil. One pan was planted with corn, sorghum and several grassy weeds. The other pan was planted with soybeans, purple nutsedge (*Cyperus rotundus*), and several broadleaf weeds. The following grassy and broadleaf species were planted: crabgrass (*Digitaria sanguinalis*), barnyardgrass (*Echinochloa crusgalli*), wild oats (*Avena fatua*), johnsongrass (*Sorghum halepense*), giant foxtail (*Setaria faberii*), Kentucky bluegrass (*Poa pratensis*), cheatgrass (*Bromus secalinus*), mustard (*Brassica arvensis*), cocklebur (*Xanthium pennsylvanicum*), pigweed (*Amaranthus retroflexus*), curly indigo (*Aeschynomene virginica*), morningglory (*ipomoea hederacea*), Cassia (*Cassia tora*), teaweed (*Sida spinosa*), velvetleaf (*Abutilon theophrasti*), and jimsonweed (*Datura stramonium*). In addition, two 12.5 cm diameter paper cups were filled with prepared soil; one was planted with rice and wheat, the other with sugarbeets. The above four containers were treated preemergence, i.e., the compounds were sprayed on the soil surface before seed germination.

Twenty-eight days after treatment, the plants were evaluated. The data obtained are summarized in Table IV. It should be noted that wheat has more tolerance for the compounds tested than most weed species.

TABLE IV

| R₁ | A | X | Z | Rate, kg/ha | Crab-grass | Barn-yard-grass | Sor-ghum | Wild oats | John-son-grass | Giant foxtail | Ky. blue-grass | Cheat-grass | Corn | Mus-tard | Cockle-bur |
|---|---|---|---|---|---|---|---|---|---|---|---|---|---|---|---|
| *(CH₃-phenyl)* | N | NHCH₃ | OCH₃ | 1/16 | 0 | 5G | 6G | 2G | 3G 3H | 4G | 5G | 5G | 5G | 0 | 0 |
|  |  |  |  | 1/4 | 4G | 8G 5H | 8G 5H | 6G | 3G 3H | 6G | 8G | 8G 5H | 6G | C | — |
| *(CH₃-phenyl)* | N | N(CH₃)₂ | OCH₃ | 1/16 | 2G | 4G | 2G | 0 | 0 | 3G | 2G | 4G | 0 | 0 | 0 |
|  |  |  |  | 1/4 | 4G | 6G 3H | 5G 3H | 6G | 3G | 6C | 6G | 6G | 5G | 7G 5H | 3G |
| *(Cl-phenyl)* | N | N(CH₃)₂ | OCH₃ | 1/16 | 5G | 4G | 5G | 0 | 3G | 5G | 6G | 6G | 2G | 7G 5C | — |
|  |  |  |  | 1/4 | 7G 3H | 7G 5H | &C | 5G | 5G 3H | 7G 5H | 8G 5H | 7G 5H | 5G 5H | 9G 9C | 0 |
| *(Cl-phenyl)* | N | NHCH₃ | OCH₃ | 1/16 | 6G | 5G 5H | 6G 3H | 4G | 6G 5H | 7G 5H | 8G | 7G | 7G 5H | 7G 3C | 0 |
|  |  |  |  | 1/4 | 8G 5C | 7G 5H | &C | 7G 3H | 7G 5H | &C | 8G | 8G 5H | 8G 5H | 8G 5C | 0 |
| *(thienyl)* | N | N(CH₃)₂ | OCH₃ | 1/16 | 2G | 0 | 0 | 0 | 0 | 0 | 0 | 0 | 0 | 6G | |
|  |  |  |  | 1/4 | 3G | 0 | 0 | 3G | 0 | 2G | 3G | 3G | 0 | 8G0 | 4G |

| R₁ | A | X | Z | Rate, kg/ha | Pig-weed | Nut-sedge | H. indigo | Morn-ing-glory | Cas-sia | Tea-weed | Vel-vet-leaf | Jim-son-weed | Soy-bean | Rice | Wheat | Sug-ar-beets | Dal-lis |
|---|---|---|---|---|---|---|---|---|---|---|---|---|---|---|---|---|---|
| *(CH₃-phenyl)* | N | NHCH₃ | OCH₃ | 1/16 | &C | 0 | — | 6G | 0 | 8G | 5G | 0 | 0 | 6G 7H | 0 | 4G 3H | |
|  |  |  |  | 1/4 | &C | 0 | — | 2G | 0 | 6G | 5G 5H | 5G | 0 | 9G 9H | 4G | 8G 5H | |
| *(CH₃-phenyl)* | N | N(CH₃)₂ | OCH₃ | 1/16 | &C | 0 | — | 0 | 0 | 0 | 0 | 0 | 0 | 6G 5H | 0 | 0 | |
|  |  |  |  | 1/4 | &C | 0 | — | 2G | 0 | 7G | 3G 5H | 4G | 2H | &C | 5G | 6G 3H | |
| *(Cl-phenyl)* | N | N(CH₃)₂ | OCH₃ | 1/16 | &C | 0 | — | 0 | &C | 0 | 0 | 0 | 0 | &H | 5G | 5G | 5G |
|  |  |  |  | 1/4 | &C | 0 | — | 6G 3H | &C | C | 3G 3C | 6G 3C | 0 | — | — | 8G 8C | 6G |
| *(Cl-phenyl)* | N | NHCH₃ | OCH₃ | 1/16 | &C | 0 | — | 4G | — | — | — | 5G | 0 | &C | 2G | 7G | 5G 5H |
|  |  |  |  | 1/4 | &C | 5G | — | &C | — | — | — | 7G 5C | 0 | &C | 5G | &C | 3G 5H |
| *(thienyl)* | N | N(CH₃)₂ | OCH₃ | 1/16 | &E | 0 | — | 0 | 0 | 0 | 0 | 0 | 0 | 5G 5H | 2G | 0 | 0 |
|  |  |  |  | 1/4 | &E | 5G | — | 5G | 5G | 6G | 7G | 0 | 2H | 8G 8H | 5G | 3G | 0 |

TEST C

Twenty-five cm-diameter plastic pots filled with Fallsington silt loam were planted with soybean, cotton, alfalfa, corn, rice, wheat, sorghum, velvetleaf (*Abutilon theophrasti*), sesbania (*Sesbania exaltata*), Cassia (*Cassia tora*), morningglory (*Ipomoea sp.*), jimsonweed (*Datura stramonium*), cocklebur (*Xanthium pennsylvanicum*), crabgrass (*Digitaria sp.*), nutsedge (*Cyperus rotundus*), barnyardgrass (*Echinochloa crusgalli*), giant foxtail (*Setaria faberii*) and wild oats (*Avena fatua*). Approximately 2½ weeks after planting, the young plants and the soil around them were sprayed overall with the test chemicals dissolved in a nonphytotoxic solvent. Fourteen days after treatment, all species were compared to untreated controls and visually rated for response to treatment. The data are presented in Table V.

This test illustrates the utility of the compounds as general postemergence herbicides.

TABLE V
| R₁ | A | X | Z | Rate, kg/ha | Soy-beans | Vel-vet-leaf | Ses-bania | Cas-sia | Cot-ton | Morn-ing-glory | Al-falfa | Jim-son-weed | Cock-lebur | Corn | Crab-grass | Rice | Nut-sedge | Barn-yard-grass | Wheat | Giant Fox-tail | Wild Oats | Sor-ghum | Yellow Rocket | Pig-weed | John-son-grass |
|---|---|---|---|---|---|---|---|---|---|---|---|---|---|---|---|---|---|---|---|---|---|---|---|---|---|
| 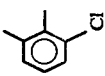 | N | N(CH₃)₂ | OCH₃ | 1/16 | 8G 5C | 5G 2H | 8C &G | 8C — | 8G 5C | 8G &G | 8G 3C | 8G 2C | 8G 5C | 7G 3U | 0 | 8G 3C | 5G | 7G 3C | 8G &G | 4G 6G | 8G &G | 6G 4U | | | |
| | | | | 1/4 | 8G 5C | 7G 5H | &G 6C | 7C | 8G 7C | &G | 8G 6C | 8G 4C | 8G 8C | 8G 4U | 3G | 8G 4C | 6G | 9G 3C | &G 3H | 6G 2C | 3C | 9G 6U | | | |

I claim:
1. A compound selected from

$$R_1-SO_2NHCNH-\underset{N=\underset{Z}{\overset{X}{\diagdown}}}{\overset{N=\underset{A}{\overset{X}{\diagup}}}{\bigg\langle}} \quad (I)$$

$$\overset{W}{\|}$$

where $R_1$ is

[benzene ring with $R_2$, $R_3$, and H substituents]

$R_2$ and $R_3$ are independently hydrogen, fluorine, chlorine, bromine, methyl, methoxy, nitro or trifluoromethyl;
W is oxygen or sulfur;
X is $-NHCH_3$ or $-N(CH_3)_2$;
Z is methyl or methoxy; and
A is N and their agriculturally suitable salts provided that when $R_2$ is nitro or trifluoromethyl, $R_3$ can not be nitro or trifluoromethyl.

2. The compound of claim 1 wherein $R_2$ is fluorine, chlorine, bromine, methyl, or nitro.

3. A compound of claim 1 wherein $R_3$ is hydrogen, fluorine, chlorine, bromine, methyl, or nitro 4. A compound of claim 1 wherein
$R_2$ is chlorine, methyl, or nitro; and
$R_3$ is hydrogen, chlorine or methyl.

5. A compound of claim 4 wherein W is oxygen.

6. A compound of claim 1 wherein
$R_2$ is chlorine, methyl, or nitro;
$R_3$ is hydrogen, chlorine or methyl; and
W is oxygen.

7. The compound of claim 1 N-[(4-methoxy-6-methylamino-1,3,5-triazin-2-yl) aminocarbonyl]-2-chlorobenzenesulfonamide.

8. The compound of claim 1 N-[(4-dimethylamino-6-methoxy-1,3,5-triazin-2-yl) aminocarbonyl]-2-chlorobenzenesulfonamide.

9. The compound of claim 1 N-[(4-dimethylamino-6-methoxy-1,3,5-triazin-2-yl) aminocarbonyl]-2-methylbenzenesulfonamide.

10. The compound of claim 1 N-[(4-methoxy-6-methylamino-1,3,5-triazin-2-yl) aminocarbonyl]-2-methylbenzenesulfonamide.

11. The compound of claim 1, N-[(4-methoxy-6-methylamino-1,3,5-triazin-2-yl)aminocarbonyl]-2-nitrobenzenesulfonamide.

12. The compound of claim 1, N-[(4-dimethylamino-6-methoxy-1,3-5-triazin-2-yl)aminocarbonyl]-2-nitrobenzenesulfonamide.

13. A composition for the control of undesirable vegetation consisting essentially of a compound of claim 1 and at least one of (a) a surface active agent and (b) a solid or liquid diluent.

14. A composition for the control of undesirable vegetation consisting essentially of a compound of claim 2 and at least one of (a) a surface-active agent and (b) a solid or liquid diluent.

15. A composition for the control of undesirable vegetation consisting essentially of a compound of claim 3 and at least one of (a) a surface-active agent and (b) a solid or liquid diluent.

16. A composition for the control of undesirable vegetation consisting essentially of a compound of claim 4 and at least one of (a) a surface-active agent and (b) a solid or liquid diluent.

17. A composition for the control of undesirable vegetation consisting essentially of a compound of claim 5 and at least one of (a) a surface-active agent and (b) a solid or liquid diluent.

18. A composition for the control of undesirable vegetation consisting essentially of a compound of claim 6 and at least one of (a) a surface-active agent and (b) a solid or liquid diluent.

19. A composition for the control of undesirable vegetation consisting essentially of the compound of claim 7 and at least one of (a) a surface-active agent and (b) a solid or liquid diluent.

20. A composition for the control of undesirable vegetation consisting essentially of the compound of claim 8 and at least one of (a) a surface-active agent and (b) a solid or liquid diluent.

21. A composition for the control of undesirable vegetation consisting essentially of the compound of claim 9 and at least one of (a) a surface-active agent and (b) a solid or liquid diluent.

22. A composition for the control of undesirable vegetation consisting essentially of the compound of claim 10 and at least one of (a) a surface-active agent and (b) a solid or liquid diluent.

23. A composition for the control of undesirable vegetation consisting essentially of the compound of claim 11 and at least one of (a) a surface-active agent and (b) a solid or liquid diluent.

24. A composition for the control of undesirable vegetation consisting essentially of the compound of claim 12 and at least one of (a) a surface-active agent and (b) a solid or liquid diluent.

25. A method for the control of undesirable vegetation which comprises of applying to the locus of such undesirable vegetation a herbicidally effective amount of a compound of claim 1.

26. A method for the control of undesirable vegetation which comprises applying to the locus of such undesirable vegetation a herbicidally effective amount of a compound of claim 2.

27. A method for the control of undesirable vegetation which comprises applying to the locus of such undesirable vegetation a herbicidally effective amount of a compound of claim 3.

28. A method for the control of undesirable vegetation which comprises applying to the locus of such undesirable vegetation a herbicidally effective amount of a compound of claim 4.

29. A method for the control of undesirable vegetation which comprises applying to the locus of such undesirable vegetation a herbicidally effective amount of a compound of claim 5.

30. A method for the control of undesirable vegetation which comprises applying to the locus of such undesirable vegetation a herbicidally effective amount of a compound of claim 6.

31. A method for the control of undesirable vegetation which comprises applying to the locus of such undesirable vegetation a herbicidally effective amount of the compound of claim 7.

32. A method for the control of undesirable vegetation which comprises applying to the locus of such undesirable vegetation a herbicidally effective amount of the compound of claim 8.

33. A method for the control of undesirable vegetation which comprises applying to the locus of such undesirable vegetation a herbicidally effective amount of the compound of claim 9.

34. A method for the control of undesirable vegetation which comprises applying to the locus of such undesirable vegetation a herbicidally effective amount of the compound of claim 10.

35. A method for the control of undesirable vegetation which comprises applying to the locus of such undesirable vegetation a herbicidally effective amount of the compound of claim 11.

36. A method for the control of undesirable vegetation which comprises applying to the locus of such undesirable vegetation a herbicidally effective amount of the compound of claim 12.

37. A method for the control of volunteer corn in soybean which comprises applying to the locus of such volunteer corn a herbicidally effective amount of a compound of claim 1.

* * * * *